US009408692B2

(12) United States Patent
Yu

(10) Patent No.: US 9,408,692 B2
(45) Date of Patent: Aug. 9, 2016

(54) ROUND OR ANATOMICAL TYPE SILICONE PROSTHESIS HAVING SHELL WITH ENHANCED DURABILITY AND METHOD FOR MANUFACTURING SAME

(71) Applicant: Won Seok Yu, Daejeon (KR)

(72) Inventor: Won Seok Yu, Daejeon (KR)

( * ) Notice: Subject to any disclaimer, the term of this patent is extended or adjusted under 35 U.S.C. 154(b) by 481 days.

(21) Appl. No.: 13/777,094

(22) Filed: Feb. 26, 2013

(65) Prior Publication Data
US 2013/0172993 A1 Jul. 4, 2013

Related U.S. Application Data

(63) Continuation of application No. PCT/KR2011/006780, filed on Sep. 14, 2011.

(30) Foreign Application Priority Data

Sep. 28, 2010 (KR) .................. 10-2010-0093850
Apr. 1, 2011 (KR) .................. 10-2011-0030363
Aug. 18, 2011 (KR) .................. 10-2011-0082393

(51) Int. Cl.
*A61F 2/12* (2006.01)
*A61L 27/18* (2006.01)
*B29C 41/14* (2006.01)

(52) U.S. Cl.
CPC . *A61F 2/12* (2013.01); *A61L 27/18* (2013.01); *B29C 41/14* (2013.01); *A61F 2250/0003* (2013.01); *A61F 2250/0036* (2013.01); *A61L 2430/04* (2013.01)

(58) Field of Classification Search
CPC ............ A61F 2/12; A61F 2250/0003; A61F 2250/0036; B29C 41/14; C08L 83/06; A61L 2430/04

USPC ................ 264/310; 427/2.24; 623/8
See application file for complete search history.

(56) References Cited

U.S. PATENT DOCUMENTS

| 6,605,116 | B2 | 8/2003 | Falcon et al. |
| 2003/0018387 | A1 | 1/2003 | Schuessler |
| 2009/0030515 | A1 | 1/2009 | Schuessler et al. |
| 2010/0178414 | A1 * | 7/2010 | Judge et al. .................. 427/2.24 |
| 2011/0046729 | A1 | 2/2011 | Schuessler et al. |

FOREIGN PATENT DOCUMENTS

| JP | 2009-96207 A | 5/2009 |
| WO | 2010/059834 A2 | 5/2010 |

OTHER PUBLICATIONS

International Search Report (PCT/KR2011/006780), WIPO, May 1, 2012.

* cited by examiner

*Primary Examiner* — Robert J Grun
(74) *Attorney, Agent, or Firm* — Park & Associates IP Law, P.C.

(57) ABSTRACT

A silicone prosthesis including a silicone shell, which has superior texture and comfort when implanted in the body, minimizes stress concentration that may arise when wearing for a long time by eliminating the difference in physical characteristics and stress in all parts of the shell, due to the silicone prosthesis having a uniform thickness, increases resistance to fatigue fracture so as to maximize the safety and lifespan of the silicone prosthesis, and which controls the flow of the silicone in various angles, thereby providing a round or an anatomical type silicone prosthesis having a shell with enhanced durability and a uniform thickness.

11 Claims, 11 Drawing Sheets

FIG. 2
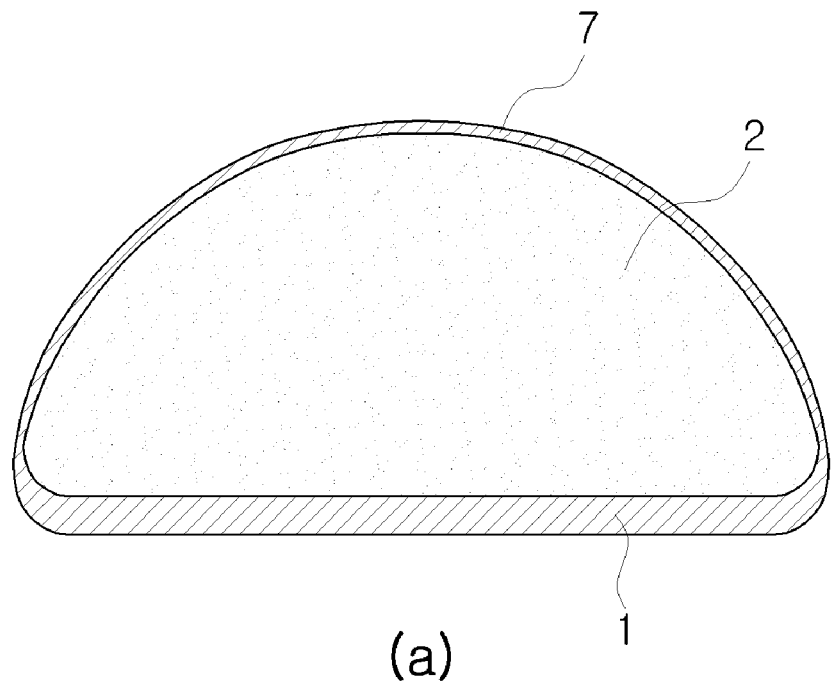
(a)
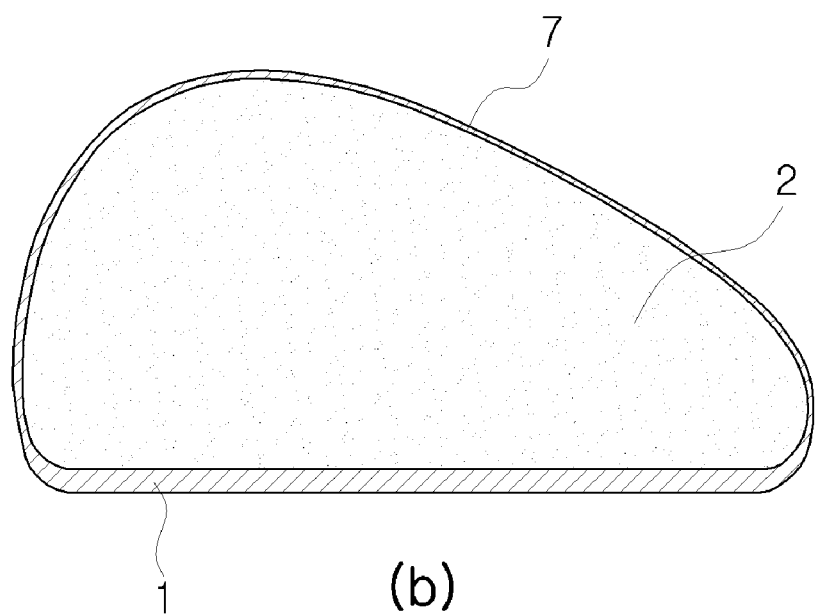
(b)

FIG. 3
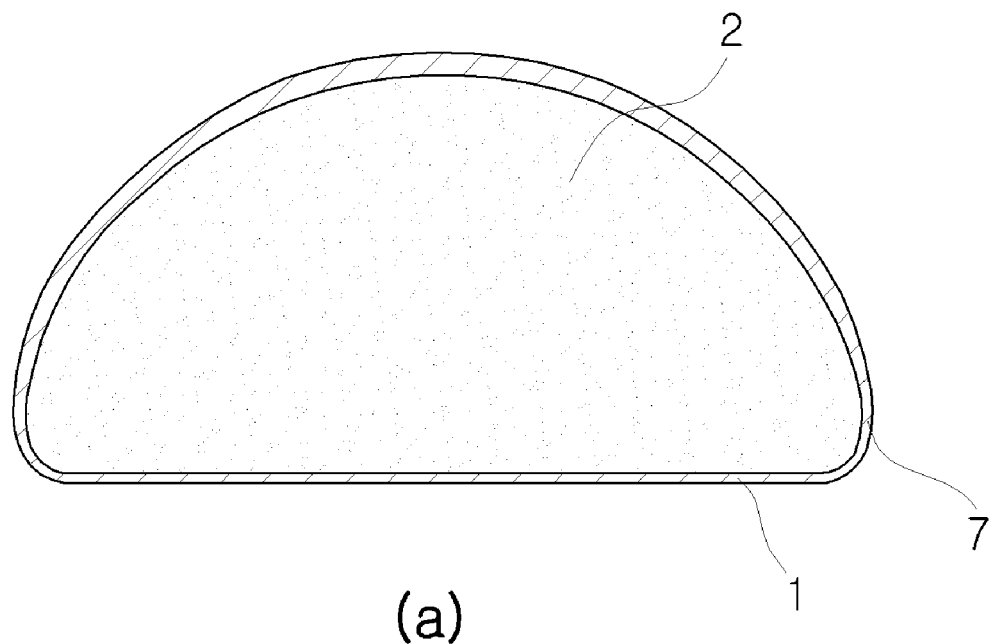
(a)
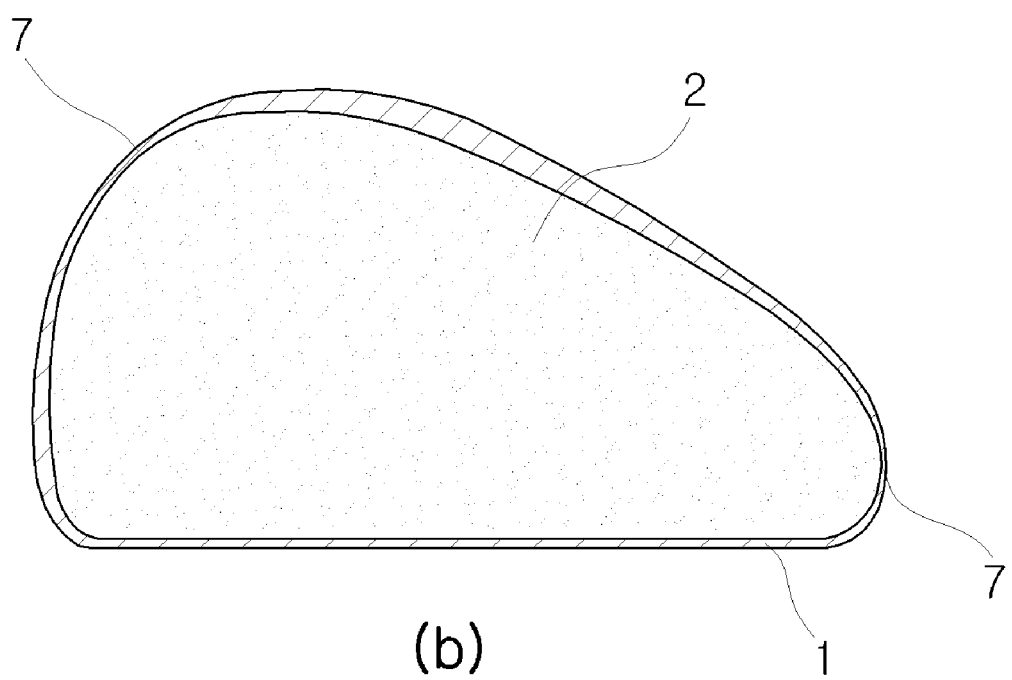
(b)

FIG. 4
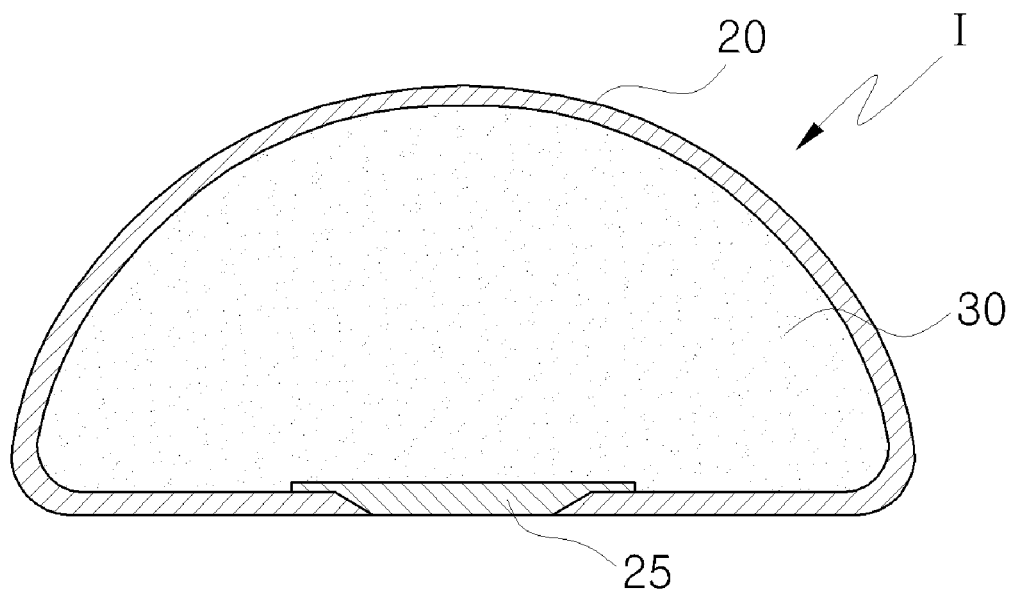
(a)
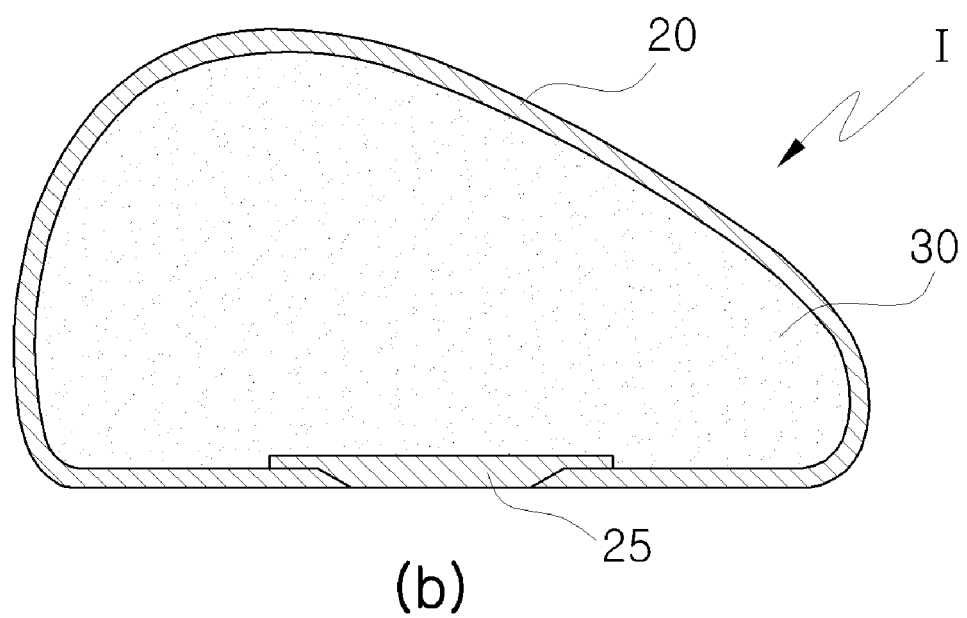
(b)

FIG. 5
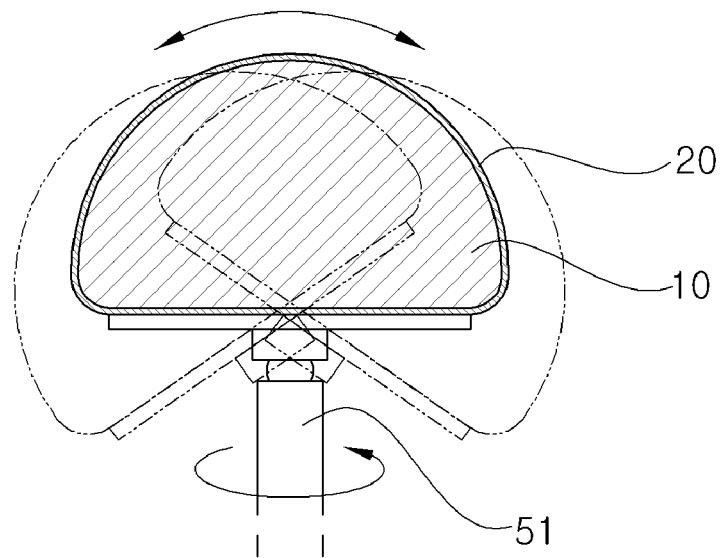
(a)
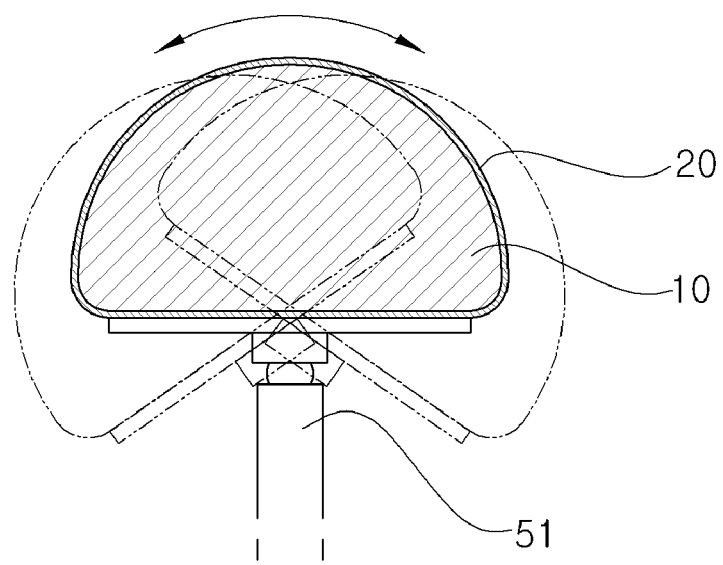
(b)

FIG. 7
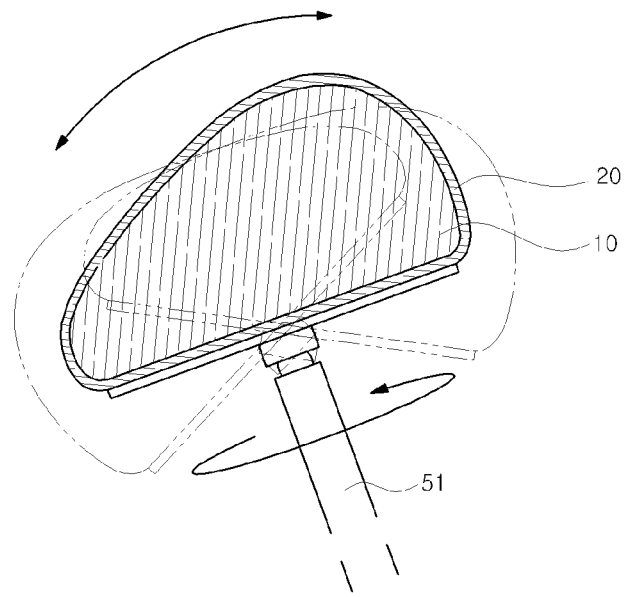
(a)
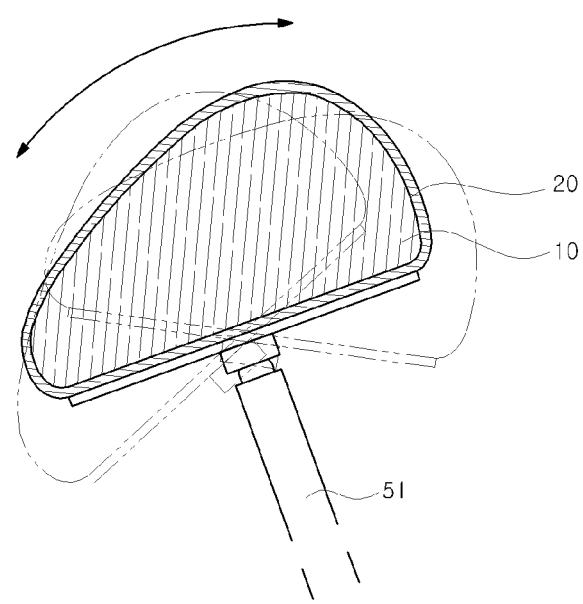
(b)

ROUND OR ANATOMICAL TYPE SILICONE PROSTHESIS HAVING SHELL WITH ENHANCED DURABILITY AND METHOD FOR MANUFACTURING SAME

REFERENCE TO RELATED APPLICATIONS

This is a continuation of pending International Patent Application PCT/KR2011/006780 filed on Sep. 14, 2011, which designates the United States and claims priority of Korean Patent Application No. 10-2010-0093850 filed on Sep. 28, 2010, Korean Patent Application No. 10-2011-0030363 filed on Apr. 1, 2011, and Korean Patent Application No. 10-2011-0082393 filed on Aug. 18, 2011, the entire contents of which are incorporated herein by reference.

FIELD OF THE INVENTION

The present invention relates to a round or anatomical type silicone prosthesis including a shell having enhanced durability and a method for manufacturing the same, and more particularly to a round or anatomical type silicone prosthesis including a shell having enhanced durability, which is manufactured such that the shell of the silicone prosthesis having a smoothly curved surface at a front side thereof is formed thin and to a constant thickness whereby the silicone prosthesis has superior texture and functions well in the body, removes differences in the thickness of the shell of the silicone prosthesis which determines the entire strength of the silicone prosthesis to minimize stress concentration after extensive use, and increases resistance to fatigue fracture to maximize safety and lifespan of the silicon prosthesis, and a method for manufacturing the same.

BACKGROUND OF THE INVENTION

In general, silicone prostheses are inserted into the human body for various purposes such as plastic surgery, and the like. As a representative example, artificial breast prostheses are used in reconstructive surgery when breast loss occurs due to diseases or accidents and in cosmetic surgery to treat a malformed breast. In terms of anatomy, artificial breast prostheses are also used for the substitution of organs or tissues.

Artificial breast prostheses are products in which a sufficient amount of a filling material, such as saline, hydro-gel, and silicone gel, is filled in an envelope formed of silicone that can be used to manufacture artificial organs (hereinafter, referred to as a "shell"), which are devices for substitution of organs in the body. These artificial breast prostheses may be classified into products according to filling materials contained therein, may be classified into round type products and anatomical type products, which are of water droplet type, according to the shape of a product, and may be classified into smooth products and textured products according to surface condition.

For example, a saline filled artificial breast prosthesis is configured such that saline is injected or is injectable into a shell formed of silicone (e.g., polydimethylsiloxane (PDMS), polydiphenylsiloxane, and polyorganosiloxane). The saline filled artificial breast prosthesis has a structure consisting of a silicone shell and a valve.

Although the saline filled artificial breast prosthesis ensures user safety even if the filling material leaks into the human body after rupture of the shell as a result of using sterile saline as the filling material, and is easy to change the volume of a breast by adjusting the injection amount of saline, the saline filled artificial breast prosthesis is significantly deteriorated to the touch after surgery as compared to other artificial breast prostheses and the shell thereof has inferior durability.

A hydro-gel filled artificial breast prosthesis is configured such that hydro-gel composed of monosaccharide and polysaccharides is filled within the shell as in the above-described saline filled artificial breast prosthesis. The hydro-gel filled artificial breast prosthesis was developed based on the principle that the filling material can be absorbed into and excreted from the human body even if the filling material leaks due to rupture of the prosthesis.

However, in the case of the hydro-gel filled artificial breast prosthesis, long-term safety has not been established, volume change over time and occurrence of wrinkles may increase after the artificial breast prosthesis is implanted, and feeling is unnatural as compared to a silicone artificial breast prosthesis. Accordingly, the hydro-gel filled artificial breast prosthesis is not currently distributed in the market as safety thereof has yet to be proven.

A silicone gel filled artificial breast prosthesis is configured such that a shell is filled with a silicone gel having an appropriate viscosity. The silicone gel filled artificial breast prosthesis has superior product durability and a more pleasant texture than the saline filled artificial breast prosthesis and thus achieves a dominant position in the market. Although the Food and Drug Administration of the United States of America (FDA) has imposed limitations on use of silicone gel filled artificial breast prostheses due to safety issues, the use of silicone gel filled artificial breast prostheses was again allowed officially in 2006.

The silicone gel filled artificial breast prosthesis has been developed in the order of a first generation prosthesis, a second generation prosthesis, and a third generation prosthesis. This development history will be described in detail as follows.

The first generation silicone gel filled artificial breast prosthesis is a product sold from the middle of the 1960s to the middle of the 1970s, and was initially developed in 1961 by Cronin and Gerow. The first generation silicone gel filled artificial breast prosthesis can be represented in brief by the use of a thick shell, a smooth surface, and a high viscosity silicone gel. This prosthesis suffers from gel bleed and capsular contracture, but a rupture speed thereof is relatively low due to the use of the thick shell.

The second generation silicone gel filled artificial breast prosthesis is a product sold from the middle of the 1970s to the middle of the 1980s, and includes a thin shell and a silicone gel filling material of a low viscosity, for the sake of smoother texture. This prosthesis is characterized by a similar gel bleed rate, higher rupture occurrence, and lower capsular contracture as compared to the first generation prosthesis.

The third generation silicone gel filled artificial breast prosthesis is a product sold from the middle of the 1980s to the present, and includes a gel bleed barrier layer to prevent gel bleed. The third generation silicone gel filled artificial breast prosthesis includes a thicker shell and silicone gel of a higher viscosity as compared to the second generation prosthesis. In addition, a product having a rough surface has been developed, in order to reduce capsular contracture.

The above-described artificial breast prostheses commonly include a shell 1, a filling material 2, and a patch bonding portion (hereinafter, referred to as "patch portion 6").

The shell 1 constituting a conventional artificial breast prosthesis is generally prepared using a dipping method or a spray method. When the shell 1 is prepared by dipping or spraying, silicone liquid is continuously flowed downward due to gravity in a drying process after dipping a mold in a silicone solution or spraying a silicone solution to a mold, and thus, the shell 1 obtained after the drying process has a thickness that increases toward a lower portion thereof as illustrated in FIG. 2. In particular, the thickness of a perimeter region of the shell 1 (generally referred to as "radius" in the art, a perimeter region having a curved surface) is very small as compared to a total thickness of the shell 1 and very large difference between the thickness of the perimeter region thereof and the thickness of upper and lower parts of the shell 1 occurs.

Such difference in thickness of each of a plurality of portions of the shell 1 causes differences in physical properties and stress (i.e., shear stress, normal stress, and torsional stress). Due to the differences in the physical properties and stress, different portions of the shell 1 undergo different degrees of elastic elongation with respect to given external pressure, and thus an elastic body such as a shell has a portion relatively vulnerable to high pressure and repeated fatigue.

Thus, artificial breast prostheses having such part relatively vulnerable to stress, i.e., a stress concentrated part 7 have limited durability and reduced lifespan due to fatigue, consequently leading to rupture of the artificial breast prostheses.

To address the problem of reduced durability of the shell, various technologies have been disclosed. U.S. Pat. No. 6,605,116B2 discloses a prosthesis configured such that the average thickness of the shell in the perimeter region is greater than the average thickness of the shell in the other regions in order to address the reduced durability of the shell occurring due to a thin perimeter portion of the shell, and a manufacturing method thereof.

US 2011/0046729A1 also discloses a prosthesis configured such that the average thickness of the shell in the perimeter region is greater than the average thickness of the shell in the other regions in order to address the reduced durability of the shell occurring due to a thin perimeter portion of the shell, and a manufacturing method thereof.

In the prostheses according to the related arts, although the thickness of the shell in the perimeter region is larger than the thickness of the shell in the other region and, accordingly, the perimeter region of the shell has stronger physical properties than the other region of the shell, there are still problems of differences in the thicknesses and physical properties of the regions of the shell. That is, the reinforced perimeter region of the shell causes differences in the thickness and physical properties of the adjacent parts of the shell, and thus the shell still has a stress concentration part, which leads to reduction in durability.

In addition, US 2010/0178414A1 discloses a method of manufacturing a shell by rotating a mold coated with a silicone solution during a drying process of the silicone solution and a device manufactured using the method.

More particularly, during the drying process of the silicone solution, the mold coated with the silicone solution is continuously rotated around an axis tilted at a certain angle with respect to a level surface, thereby changing a flow direction of the silicone solution and controlling movement of the silicone solution. Accordingly, the silicone solution is uniformly dispersed thereon and a shell having a uniform thickness is obtained.

The manufacturing method of the shell using the rotation method can reduce a difference in thicknesses of upper and lower parts of the shell 1 and a difference in thickness of the perimeter region of the shell 1 as compared to the manufacturing method of the shell without using the rotation method.

As illustrated in FIG. 3, however, it is impossible to completely eliminate a difference in the thicknesses of all the parts of the shell 1.

From a rheological point of view, the above-described manufacturing method does not take into consideration a three-dimensional structure of a mold having different slopes in regions thereof. From the rheological point of view, a difference in flow rate of the silicone solution in each region of the mold occurs according to the three-dimensional structure of the mold having slope variation in each region thereof. Thus, the thickness of an upper part of the shell is larger than that of a lower part of the shell and thickness difference in each region of the shell occurs according to the three-dimensional structure of the mold.

In addition, as to rotational velocity and the viscosity of the silicone solution, the mold is continuously rotated around a rotation axis, and thus, difference in flow rate of the silicone solution in each region of the mold may occur according to a separation distance of the silicone solution from the rotation axis, whereby the thickness of the shell may increase based on the rotation axis.

Such thickness difference further increases due to increased surface area of the mold used as the size of products increases.

Actually, a round type shell 1 manufactured using the conventional rotation method is configured as illustrated in FIG. 3 such that the thickness of an upper part of the shell 1 is larger than that of a lower part of the shell 1. In addition, as illustrated in FIG. 3(b), an anatomical type shell 1 is also formed as the round type prosthesis 1 such that the thickness of an upper part thereof is greater than that of a lower part thereof. In addition, due to a three-dimensional structure of a mold in which left and right sides of the mold are asymmetrical, thickness difference occurs such that the thickness of one side of an upper inclined plane of the mold is generally very small, while the thickness of the other side thereof is very large, and thus the stress concentration part 7 relatively vulnerable to stress is still formed on the shell 1. In addition, conventional artificial breast prostheses have been used with existing problems being unsolved, i.e., high risk of fatigue fracture due to limitation on durability when used.

SUMMARY OF THE INVENTION

Therefore, the present invention has been made in view of the above problems, and it is an object of the present invention to provide a round or anatomical type silicone prosthesis having a shell with enhanced durability in which a thickness difference is removed such that a silicone shell forming an outer appearance of the silicone prosthesis has an entirely uniform thickness, and thus, differences in physical properties and stress are removed and therefore stress concentration is minimized, resistance to fatigue fracture is minimized, there is no deformation of or damage to products even after long-term use of the silicone prosthesis and thus the reliability of the silicone prosthesis increases and safety and lifespan thereof are maximized, and a method for manufacturing the same.

It is another object of the present invention to provide a round or anatomical type silicone prosthesis having a shell with enhanced durability which has a smoothly and forwardly curved surface and a uniform and small thickness and thus has superior texture and excellent comfort when implanted into the body, thereby achieving improved product quality, and a method of manufacturing the same.

It is a further object of the present invention to provide a round or anatomical type silicone prosthesis having a shell with enhanced durability in which most of the existing manufacturing processes limited by manual work are automated, which results in reduced personnel expenses, convenience of operation, quality reproducibility, and maximized product quality.

In accordance with an aspect of the present invention, the above and other objects can be accomplished by the provision of a round or anatomical type silicone prosthesis including a silicone shell, the silicone shell having an entirely uniform thickness through control of the flow of silicone in various angles and having enhanced durability.

The silicone prosthesis may have an entirely uniform thickness such that deviation between an average thickness of the thickest part of the silicone shell and an average thickness of the thinnest part of the silicone shell is 1 to 15%.

In accordance with another aspect of the present invention, there is provided a method of manufacturing a round or anatomical type silicone prosthesis including a silicone shell with enhanced durability by coating a silicone solution on a mold body having a shape of the silicone prosthesis and drying the coated mold body in a drying device to form the silicone shell, the method including a silicone thickness adjustment step performed such that a jig is disposed in an inner space of the drying device to fix the mold body, the mold body is fixed to the jig, and the jig is maintained in a level state and then moved by rotation and tilting at various angles to uniformly adjust the thickness of the silicone shell using fluidity of silicone.

In the silicone thickness adjustment step, the jig of the drying device may be periodically or non-periodically moved in a tilted state at a predetermined angle in all directions including front, rear, left and right directions while continuously rotating the mold body on the same level line.

In the silicone thickness adjustment step, the jig of the drying device may be periodically or non-periodically moved in a tilted state at a predetermined angle in all directions including front, rear, left and right directions while fixing the mold body in a level state.

In the silicone thickness adjustment step, the jig of the drying device may further include a jig displacement configuration such that the jig rotates by itself at a rotation angle ranging from 1 to 360° and is continuously rotated by repeating a temporary stop at every determined angle within 1 to 180° among rotation displacements for a certain period of time.

In the silicone thickness adjustment step, the jig of the drying device may be periodically or non-periodically moved in a tilted state at a predetermined angle in all directions including front, rear, left and right directions while continuously rotating the mold body on the same level line in a tilted state at a constant angle toward any one of the all directions.

In the silicone thickness adjustment step, the jig of the drying device may be periodically or non-periodically moved in a tilted state at a predetermined angle in all directions including front, rear, left and right directions without rotation in a state of the mold body being tilted at a constant angle in any one of the all directions.

The jig of the drying device may be tilted at 10 to 60° based on a level surface in a direction in which the mold body is to be tilted.

The method may comprise a silicone solution coating step to coat the mold body with the silicone solution by immersing the mold body having a shape of the silicone prosthesis in a vessel filled with a sufficient amount of the silicone solution or spraying the silicone solution onto the mold body, a silicone thickness adjustment step to uniformly adjust the thickness of the silicone shell by operating the jig inside the drying device to which the mold body is fixed and to dry the coated silicone solution, a silicone etching step to define upper and lower spaces of the drying device using a barrier member included in the drying device and to spray an organic chemical solution onto the silicone shell through a microsprayer, a silicone hardening step to harden the resulting mold body to form into the silicone shell, a mold separation step to separate the silicone shell from the mold body through a perforated lower surface portion of the silicone shell, and a prosthesis formation step to attach a patch part to the perforated lower surface portion so as to close an inner space of the silicone shell from the outside and to inject a filling material into the inner space of the silicone shell.

The drying device may be configured such that dry air is uniformly blown from all directions including up, down, left and right directions through an air blower and the method may further comprise setting a temperature difference between upper and lower spaces of the drying device such that temperatures in the upper and lower spaces are differently adjusted.

The drying device may control a drying rate of the silicone shell by adjusting an amount and velocity of air from the air blower and thus the thickness of the silicone shell may be entirely adjusted.

The organic chemical solution used in the silicone etching step may be at least one of xylene, toluene, benzene, and a cyclic aromatic compound.

The microsprayer used in the silicone etching step may include at least one microsprayer disposed in the lower space of the drying device at a position in which the organic chemical solution is uniformly sprayed onto the silicone shell so that thickening of the silicone shell from a lower surface thereof is prevented during drying.

The drying device may adjust a concentration of the organic chemical solution sprayed from the microsprayer as needed.

The drying device may be configured such that a volatilization direction of the organic chemical solution sprayed from the microsprayer is changed and adjusted by adjusting a direction of dry air from an air blower.

The method may further include an air spray step between the silicone solution coating step and the silicone hardening step, to completely attach the silicone solution coated on the mold body to the mold body in accordance with the shape thereof through a high pressure air nozzle.

BRIEF DESCRIPTION OF THE DRAWINGS

The above and other objects, features and other advantages of the present invention will be more clearly understood from the following detailed description taken in conjunction with the accompanying drawings, in which:

FIGS. 2(a) and 2(b) are sectional views schematically illustrating a round silicone prosthesis and an anatomical type silicone prosthesis, respectively, which are manufactured using a conventional simple drying method;

FIGS. 3(a) and 3(b) are schematic sectional views of a round type silicone prosthesis and an anatomical type silicone prosthesis, respectively, which are manufactured using a conventional rotary drying method;

FIGS. 4(a) and 4(b) are sectional views respectively illustrating round and anatomical type silicone prostheses according to embodiments of the present invention;

FIGS. 5(a) and 5(b) are views illustrating operation states of a jig used in a silicone thickness adjustment step of a manufacturing method of the round type silicone prosthesis according to the embodiment of the present invention;

FIGS. 7(a) and 7(b) are views illustrating operation states of a jig used in a silicone thickness adjustment step of a manufacturing method of the anatomical type silicone prosthesis according to the embodiment of the present invention;

DETAILED DESCRIPTION OF THE INVENTION

Figure 1:
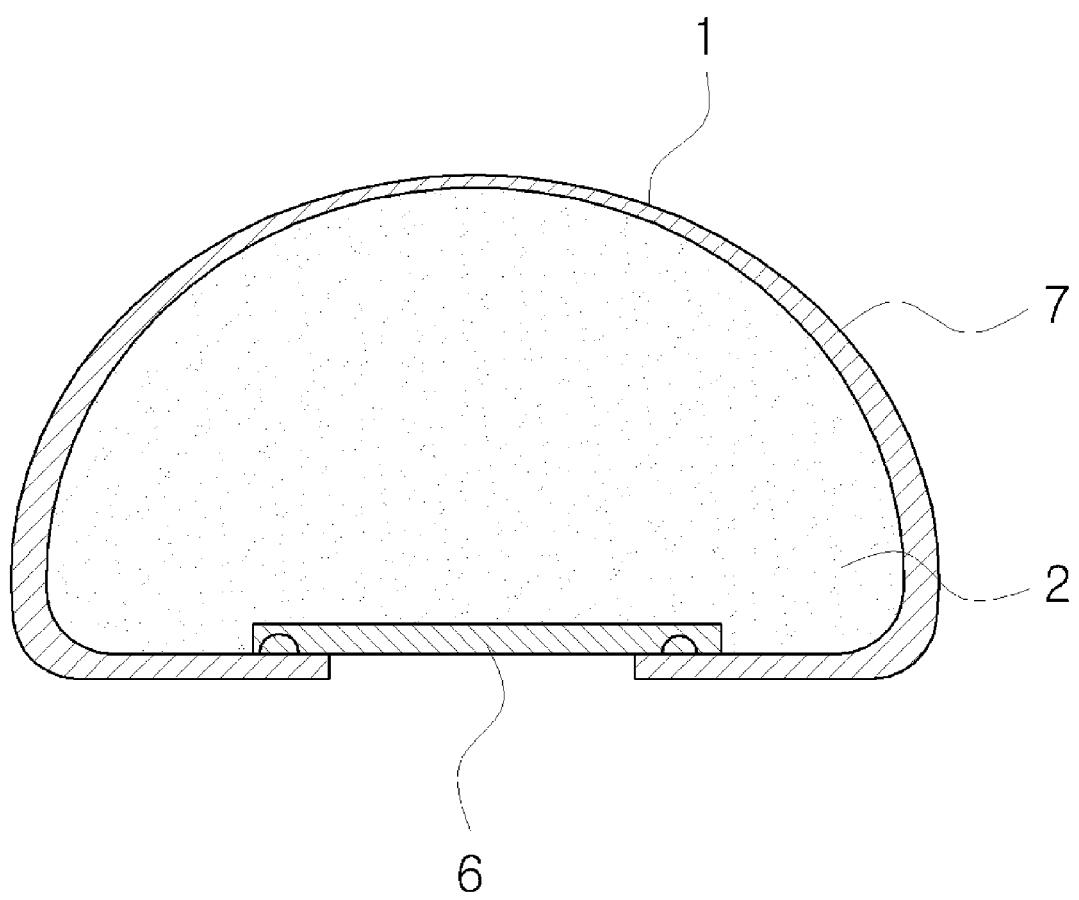
FIG. 1 is a sectional view schematically illustrating configuration of a conventional silicone prosthesis.

According to an embodiment of the present invention, a round or anatomical type silicone prosthesis includes a silicone shell that has an entirely uniform thickness through control of the flow of silicone in various angles and has enhanced durability.

The round or anatomical type silicone prosthesis has an entirely uniform thickness such that deviation between an average thickness of the thickest part of the silicone shell and an average thickness of the thinnest part of the silicone shell is 1 to 15%.

According to another embodiment of the present invention, a method of manufacturing a round or anatomical type silicone prosthesis including a silicone shell with enhanced durability by coating a silicone solution on a mold body having a shape of the silicone prosthesis and drying the coated mold body in a drying device to form the silicone shell includes a silicone thickness adjustment step performed such that a jig is disposed in an inner space of the drying device to fix the mold body, the mold body is fixed to the jig, and the jig is maintained in a level state and then moved by rotation and tilting at various angles to uniformly adjust the thickness of the silicone shell using fluidity of silicone.

In the silicone thickness adjustment step, the jig of the drying device is periodically or non-periodically moved in a tilted state at a predetermined angle in all directions including front, rear, left and right directions while continuously rotating the mold body on the same level line.

In the silicone thickness adjustment step, the jig of the drying device is periodically or non-periodically moved in a tilted state at a predetermined angle in all directions including front, rear, left and right directions while fixing the mold body in a level state.

In the silicone thickness adjustment step, the jig of the drying device further includes a jig displacement configuration such that the jig rotates by itself at a rotation angle ranging from 1 to 360° and is continuously rotated by repeating a temporary stop at every determined angle within 1 to 180° among rotation displacements for a certain period of time.

In the silicone thickness adjustment step, the jig of the drying device may be periodically or non-periodically moved in a tilted state at a predetermined angle in all directions including front, rear, left and right directions while continuously rotating the mold body on the same level line in a tilted state at a constant angle toward any one of the all directions.

In the silicone thickness adjustment step, the jig of the drying device is periodically or non-periodically moved in a tilted state at a predetermined angle in all directions including front, rear, left and right directions without rotation in a state of the mold body being tilted at a constant angle in any one of the all directions.

The jig of the drying device is tilted at 10 to 60° based on a level surface in a direction in which the mold body is to be tilted.

The method may comprise a silicone solution coating step to coat the mold body with the silicone solution by immersing the mold body having a shape of the silicone prosthesis in a vessel filled with a sufficient amount of the silicone solution or spraying the silicone solution onto the mold body, a silicone thickness adjustment step to uniformly adjust the thickness of the silicone shell by operating the jig inside the drying device to which the mold body is fixed and to dry the coated silicone solution, a silicone etching step to define upper and lower spaces of the drying device using a barrier member included in the drying device and to spray an organic chemical solution onto the silicone shell through a microsprayer, a silicone hardening step to harden the resulting mold body to form into the silicone shell, a mold separation step to separate the silicone shell from the mold body through a perforated lower surface portion of the silicone shell, and a prosthesis formation step to attach a patch part to the perforated lower surface portion so as to close an inner space of the silicone shell from the outside and to inject a filling material into the inner space of the silicone shell.

The drying device is configured such that dry air is uniformly blown from all directions including up, down, left and right directions through the air blower and the method further comprises setting a temperature difference between upper and lower spaces of the drying device such that temperatures in the upper and lower spaces are differently adjusted.

The drying device controls a drying rate of the silicone shell by adjusting an amount and velocity of air from the air blower and thus the thickness of the silicone shell is entirely adjusted.

The organic chemical solution used in the silicone etching step includes at least one of xylene, toluene, benzene, and a cyclic aromatic compound.

The microsprayer used in the silicone etching step includes at least one microsprayer disposed in the lower space of the drying device at a position in which the organic chemical solution is uniformly sprayed onto the silicone shell so that thickening of the silicone shell from a lower surface thereof is prevented during drying.

The drying device adjusts a concentration of the organic chemical solution sprayed from the microsprayer as needed.

The drying device is configured such that a volatilization direction of the organic chemical solution sprayed from the microsprayer is changed and adjusted by adjusting a direction of dry air from an air blower.

The method may further include an air spray step between the silicone solution coating step and the silicone hardening step, to completely attach the silicone solution coated on the mold body to the mold body in accordance with the shape thereof through a high pressure air nozzle.

Hereinafter, a method of manufacturing a silicone prosthesis having a shell with enhanced durability, according to an exemplary embodiment of the present invention, will be described in detail with reference to the accompanying drawings.

However, the present invention may be embodied in many different forms and should not be construed as being limited to embodiments set forth herein. Rather, these embodiments are provided so that this disclosure will fully convey the scope of the invention to those skilled in the art, and shapes of elements illustrated in the drawings are provided for illustrative purposes and clarity only.

According to an embodiment of a round or anatomical type silicone prosthesis having a shell with enhanced durability includes, as illustrated in FIG. 4, a silicone prosthesis I includes a silicone shell 20. The silicone shell 20 has an entirely uniform thickness.

In detail, the silicone prosthesis I includes the silicone shell 20 that forms an outer wall of the silicone prosthesis I, a patch part 25 attached to a smooth lower surface of the silicone shell 20, and a filling material 30 filling an inner space of the silicone shell 20.

The patch part 25 includes an inlet sealing portion (not shown) so as to close a fine hole formed in a process of injecting the filling material 30 into the inner space of the silicone shell 20.

The silicone prosthesis I may be of a round type or an anatomical type. That is, the round silicone prosthesis I is smoothly rounded forward and has a hemispherical shape, and the anatomical type silicone prosthesis I has a teardrop shape such that the anatomical type silicone prosthesis has a forwardly curved surface that is biased to one side.

The silicone prosthesis I has a uniform thickness through control of the flow of silicone in various angles.

The silicone prosthesis I has an entirely uniform thickness such that the silicone shell 20 has a thickness deviation of 1 to 15%. That is, a deviation between an average thickness of the thickest portions of the silicone shell 20 and an average thickness of the thinnest portions of the silicone shell 20 is constant, i.e., 1 to 15%.

Figure 6:
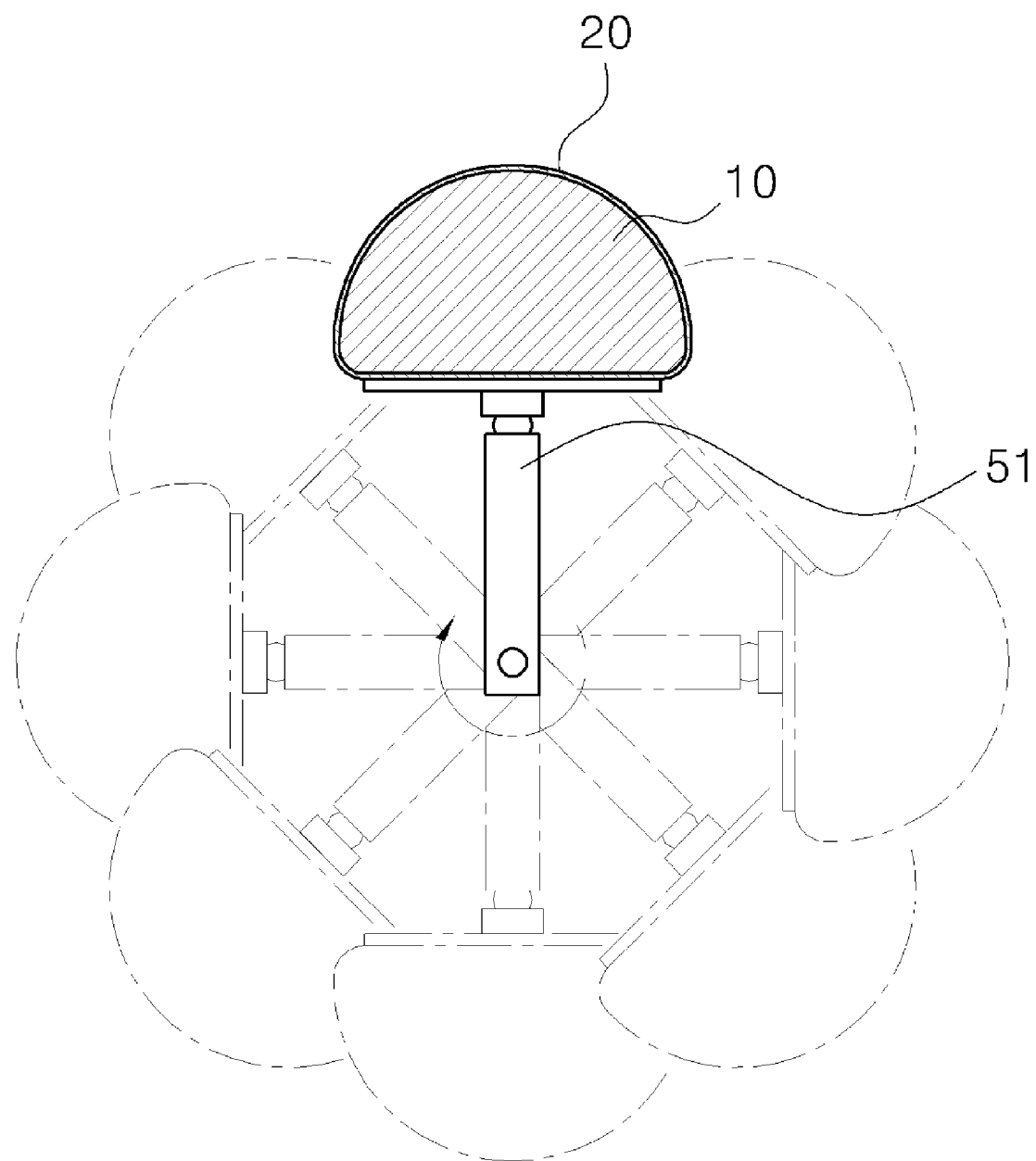
FIG. 6 is a view illustrating application of jig displacement implemented in manufacturing the round or anatomical type silicone prosthesis according to the embodiment of the present invention.

According to another embodiment of the present invention, as illustrated in FIGS. 5 through 7, a method of manufacturing the round or anatomical type silicone prosthesis having a shell with enhanced durability by coating a silicone solution 5 on a mold body 10 and drying the mold body 10 in a drying device 50 to form the silicone shell 20 of the silicone prosthesis I includes a silicone thickness adjustment step (S20) of adjusting the thickness of the silicone shell 20.

In the silicone thickness adjustment step (S20), the silicone solution 5, which is a raw material, is uniformly coated on the mold body 10 having a shape corresponding to that of the silicone prosthesis I such that the coating process is performed in various directions so that the silicone solution 5 flows along the surface of the mold body 10 in all directions before hardening, whereby the thickness of the silicone shell 20 is uniformly adjusted.

The silicone thickness adjustment step (S20) is performed in the drying device 50. In particular, a jig 51 is formed inside the drying device 50 to fix the mold body 10 coated with the silicone solution 5.

In the silicone thickness adjustment step (S20), it is possible to drive the jig 51 by setting operation and movement thereof according to types of the silicone prosthesis I. That is, in the silicone thickness adjustment step (S20), the jig 51 is configured such that the jig 51 is correspondingly operated according to the types of the silicone prosthesis I, i.e., the round silicone prosthesis and the anatomical type silicone prosthesis.

First, operation types of the jig 51 in the silicone thickness adjustment step (step S20) for manufacturing the round and anatomical type silicone prostheses I will be described with reference to FIGS. 5 and 6.

In the silicone thickness adjustment step (step S20) for manufacturing the round and anatomical type silicone prostheses I, as illustrated in FIG. 5, the mold body 10 is fixed to the jig 51 and the jig 51 is maintained in a horizontal state and then is rotated and tilted at various angles to control the flow of silicone so that the thickness of the silicone shell 20 is uniformly adjusted.

In the silicone thickness adjustment step (step S20), the jig 51 of the drying device 50 is moved in a tilted state at a predetermined angle in all directions including forward and backward and in left and right directions so that the silicone solution 5 is uniformly coated over the entire area of the surface of the mold body 10.

The jig 51 may be moved such that the mold body 10 is tilted periodically. Also, the jig 51 may be moved such that the mold body 10 is tilted non-periodically.

In the silicone thickness adjustment step (step S20), as illustrated in FIG. 5(a), the jig 51 of the drying device 50 may be periodically or non-periodically moved in a tilted state at a predetermined angle in all the directions while continuously rotating the mold body 10 on the same horizontal line.

In addition, as illustrated in FIG. 5(b), the jig 51 of the drying device 50 may be periodically or non-periodically moved in a tilted state at a predetermined angle in all directions while fixing the mold body 10 in a level state. That is, the jig 51 is configured so as to tilt the mold body 10 at the same angle and maintain the mold body 10 in a non-rotation state in which the mold body 10 does not rotate on the same horizontal line.

To the jig 51 may be applied a structure of a robot arm generally used in automobile manufacturing processes and a sand coating process for molding or a structure of nutator equipment (e.g., nutator mixer and the like), and thus, a detailed description thereof is not provided here.

A tilting angle of the jig 51 may be arbitrarily determined, but is preferably 10 to 60°. Alternatively, tilting angles of the jig 51 in front, rear, left and right directions may be differently set.

For example, as the size of the silicone prosthesis I to be manufactured increases, the size of the mold body 10 used also increases, which leads an increase in the surface area of the mold body 10 and amount of the silicone solution 5 used for coating, and thus, the tilting angle of the jig 51 may be set at 25° when a 200 cc silicone prosthesis is manufactured and may be set at 30° when a 600 cc silicone prosthesis is manufactured.

Also, in the silicone thickness adjustment step (step S20) for manufacturing the round or anatomical type silicone prosthesis I, as illustrated in FIG. 6, the jig 51 of the drying device 50 may also perform jig displacement through rotation of the jig 51 by itself.

The jig 51 of the drying device 50 moves by repeatedly rotating upward and downward at an angle ranging from 1 to 360°.

The jig 51 of the drying device 50 is configured such that the jig 51 is continuously rotated by repeating a temporary stop for a certain period of time at every angle set within 1 to 180° while changing positions through upward and downward rotation.

For example, the jig displacement is performed in the silicone thickness adjustment step (step S20) such that when an angle for temporary stop is set to 45°, the jig 51 rotates by itself, is stopped at every 45°, and maintained in the stopped state for a certain period of time (e.g., about 30 seconds to 1 minute), to provide a time to enable the silicone solution 5 to sufficiently flow at the corresponding angle, whereby the thickness of the silicone shell 20 is uniformly adjusted.

Hereinafter, an operation type of the jig 51 in the silicone thickness adjustment step (step S20) for manufacturing the anatomical type silicone prosthesis I will be described in detail with reference to FIG. 7.

In the silicone thickness adjustment step (step S20), as illustrated in FIG. 7(*a*), the jig 51 of the drying device 50 is configured such that the jig 51 is periodically or non-periodically moved in a tilted state at a predetermined angle in all directions including front, rear, left and right directions while continuously rotating the mold body 10 on a horizontal line in a tilted state at a constant angle in any one of the all directions.

In the silicone thickness adjustment step (step S20), as illustrated in FIG. 7(*b*), the jig 51 of the drying device 50 is configured such that the jig 51 is periodically or non-periodically moved in a tilted state at a predetermined angle in all directions including front, rear, left and right directions without rotation in a tilted state at a constant angle toward any one of the all directions.

The tilting direction of the mold body 10 may vary according to a direction in which the silicone shell 20 is biased.

The jig 51 of the drying device 50 may be tilted at 1 to 90° in a direction in which the mold body 10 is biased, preferably, at 10 to 60°.

That is, in manufacture of the anatomical type silicone prosthesis I, the jig 51 may be manufactured such that the angle of the jig 51 is set according to a three-dimensional structure of the mold body 10.

As described above, by movement of the jig 51 in rotated and tilted states through the silicone thickness adjustment step (step S20), the jig 51 is moved in a tilted state at various angles, with continuous rotation or without rotation, and thus, flow directions of the silicone solution 5 are variously embodied, whereby the thickness of the silicone shell 20 may be more uniformly adjusted.

In addition, the silicone shell 20 is dried using the jig 51 correspondingly operated according to the types of the silicone prosthesis I: round type and anatomical type, and thus, various types of silicone prostheses may be smoothly manufactured and the thicknesses of silicone shells of the silicone prostheses may be uniformly adjusted.

In addition, the silicone shell 20 is manufactured by applying the corresponding operation of the jig 51 according to product types and sizes of the round silicone prosthesis and the anatomical type silicone prosthesis, and thus, various shapes of silicone prostheses I may be smoothly manufactured and the thickness of the silicone shell 20 may also be uniform regardless of various shapes and sizes of products.

Figure 8:
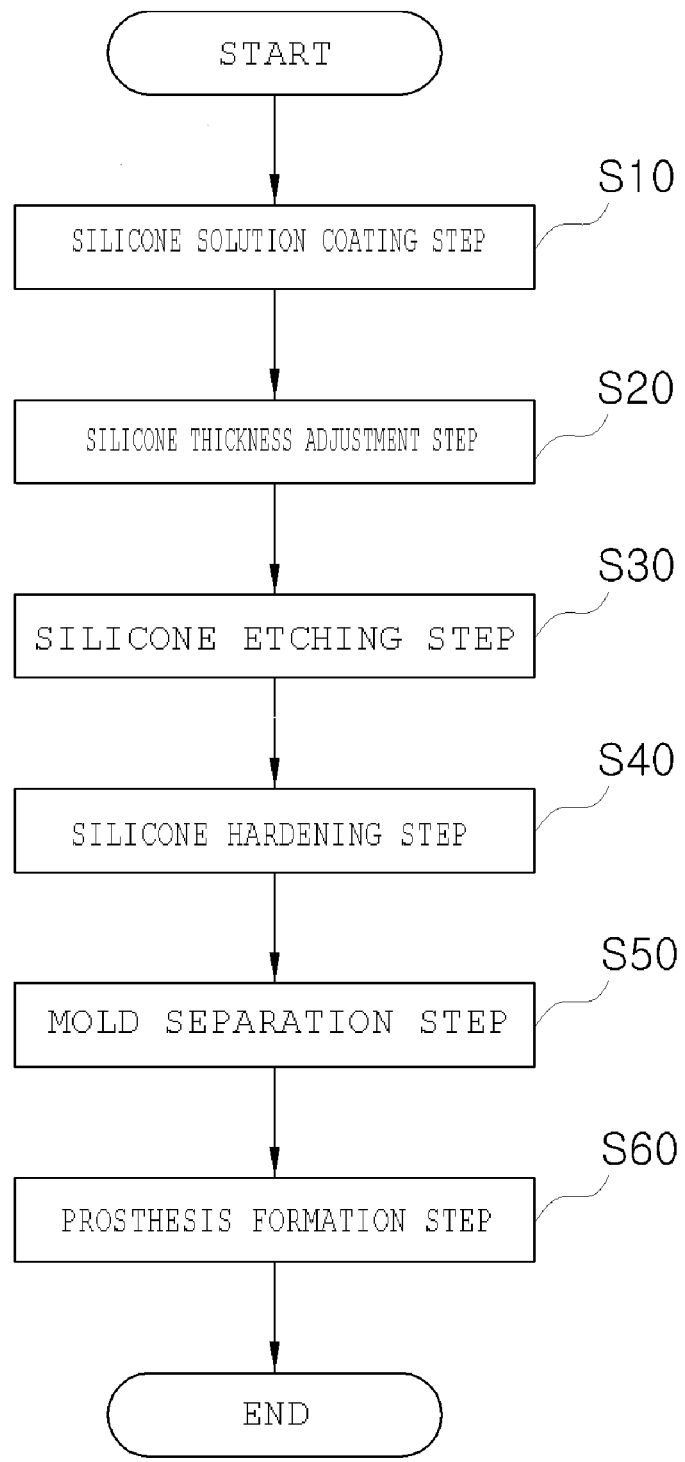
FIG. 8 is a flowchart illustrating a round or anatomical type silicone prosthesis manufacturing method according to an embodiment of the present invention.
Figure 9:
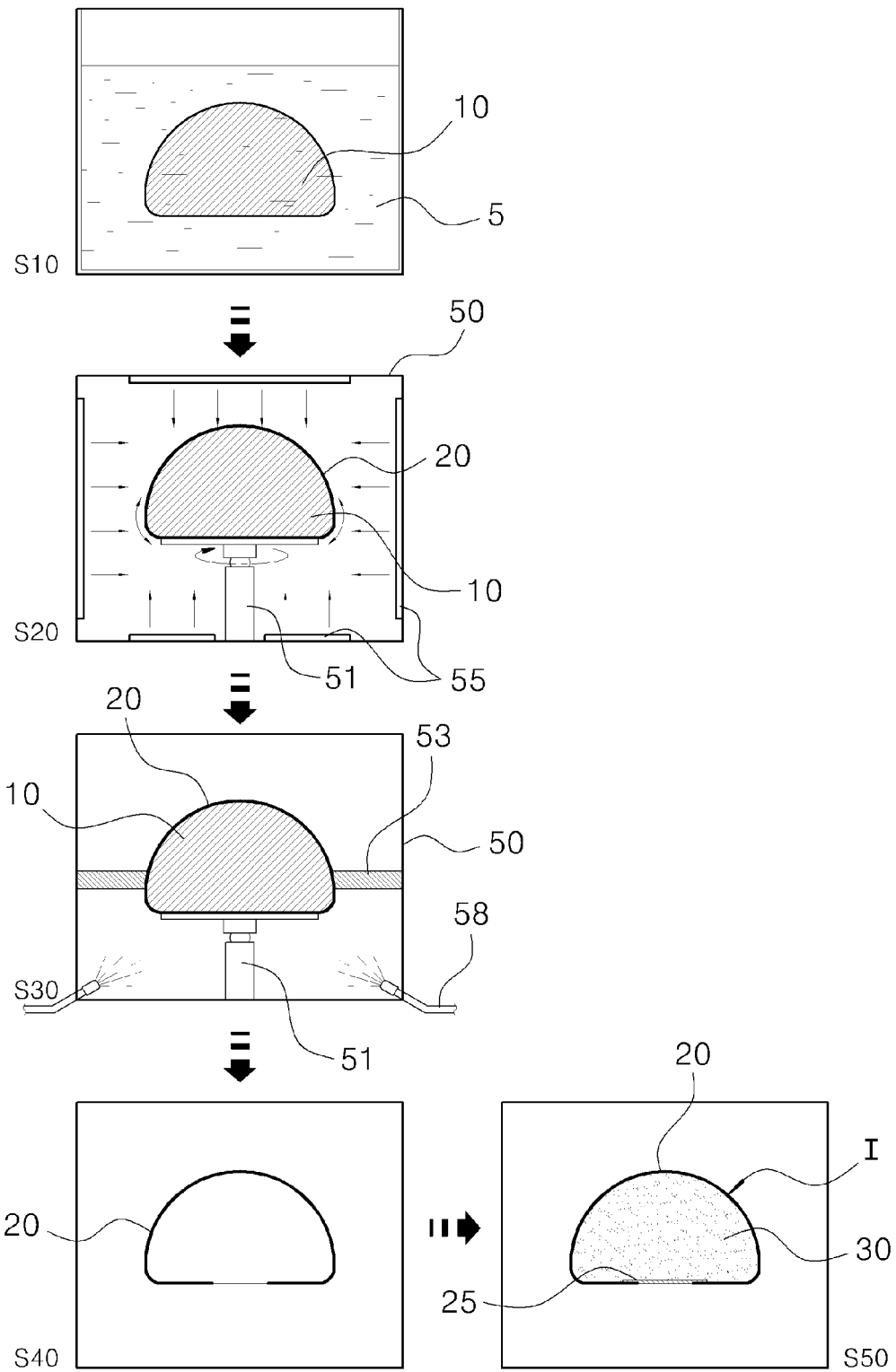
FIG. 9 depicts views sequentially illustrating the manufacturing method according to the embodiment of the present invention.

The method of manufacturing the round or anatomical type silicone prosthesis having a shell with enhanced durability may include, as illustrated in FIGS. 8 and 9, a silicone solution coating step (step S10), a silicone thickness adjustment step (step S20), a silicone etching step (step S30), a silicone hardening step (step S40), a mold separation step (step S50), and a prosthesis formation step (step S60).

In the silicone solution coating step (step S10) which is an initial process for obtaining a silicone prosthesis I, the mold body 10 having a shape of the silicone prosthesis I is immersed in a vessel filled with the silicone solution 5 or the silicone solution 5 is sprayed onto the mold body 10, thereby coating the mold body 10 with the silicone solution 5.

Before the mold body 10 is immersed in the vessel containing the silicone solution 5 or the silicone solution 5 is sprayed onto the mold body 10, a process for removing impurities (dust and the like) on an outer surface of the mold body 10 may be performed using an air gun, or the like.

Also, before immersion of the mold body 10 in the silicone solution 5 or spraying of the silicone solution 5 thereonto, a process for removing impurities on the mold body 10 using washing water may be performed. After the impurities on the mold body 10 are removed by immersing the mold body 10 in the washing water, the washing water remaining on the mold body 10 may be removed by air blowing.

In the silicone thickness adjustment step (step S20), the silicone solution 5 coated on the mold body 10 through the silicone solution coating step (step S10) is dried to form the silicone shell 20. More particularly, in the silicone thickness adjustment step (step S20), the mold body 10 coated with the silicone solution 5 is taken out of the vessel and then the silicone solution 5 is dried using the drying device 50. In this regard, the mold body 10 is fixed on the jig 51 inside the drying device 50 and the silicone solution 5 is dried using dry air having a predetermined temperature, generated from an air blower 55, to form the silicone shell 20.

In the silicone thickness adjustment step (step S20), before the silicone solution 5 is completely dried to form the silicone shell 20, a process of uniformly adjusting the thickness of the silicone shell 20 may be performed through operation of the jig 51.

The drying device 50 used in the silicone thickness adjustment step (step S20) uniformly blows dry air from up, down, left and right directions via the air blower 55.

Also, the manufacturing method may further include setting temperatures of dry air from the air blower 55 to be differently adjusted in upper and lower spaces inside the drying device 50.

As described above, when the upper and lower spaces inside the drying device 50 have temperature differences, temperature differences occur at upper and lower surfaces of the mold body 10 coated with the silicone solution 5 and it may be possible to separately control drying rates of upper and lower portions of the silicone solution 5 coated on the mold body 10.

The drying device 50 controls the drying rate of the silicone shell 20 by adjusting the amount and velocity of dry air from the air blower 55, and thus, the thickness of the silicone shell 20 may be entirely adjusted.

For example, in the silicone thickness adjustment step (step S20), when the silicone shell 20 needs to be formed relatively thick, the amount and velocity of dry air from the air blower 55 may be set large to rapidly dry the coated silicone solution 5. Thus, the silicone solution 5 coated on the mold body 10 through the silicone solution coating step (step S10) is entirely formed into the silicone shell 20 without loss of the amount of the silicone solution 5. On the other hand, when the silicone shell 20 needs to be relatively thin, the drying rate of the silicone solution 5 is adjusted to be slow by reducing the amount and velocity of air from the air blower 55, whereby the silicone shell 20 has a small thickness. That is, the drying rate of the silicone solution 5 is controlled by adjusting the amount and velocity of air from the air blower 55, whereby the thickness of the silicone shell 20 is adjusted.

In the silicone etching step (step S30), an organic chemical solution is uniformly sprayed onto the silicone shell 20 using separate microsprayers 58 disposed at a lower portion of the drying device 50. More particularly, in a general case of drying a silicone solution, the silicone solution is hardened by flowing down by gravity during the drying process, but, in this embodiment, the silicone shell 20 may be hardened to a primarily uniform thickness through changes in operation and position of the jig 51 in the silicone thickness adjustment step (step S20), and then the organic chemical solution is sprayed onto the silicone shell 20 in the silicone etching step (step S30) to remove portions of the silicone shell 20 having non-uniform thicknesses, whereby the thickness of the silicone shell 20 is entirely uniform.

In the silicone etching step (step S30), the organic chemical solution is sprayed onto the silicone shell 20 having been dried in the silicone thickness adjustment step (step S20) through the microsprayers 58, and thus, a portion (i.e., a portion having a relatively large thickness) of the silicone shell 20 is smoothly etched, whereby the silicone shell 20 has a uniform thickness. Alternatively, the organic chemical solution may be sprayed onto the silicone shell 20 through the microsprayers 58 before the silicone shell 20 is hardened, to increase fluidity of the silicone solution 5 and enable the silicone solution 5 to flow down, whereby the thickness of the silicone shell 20 is kept constant.

A barrier member 53 is included inside the drying device 50 to define an upper space and a lower space. That is, the barrier member 53 allows the organic chemical solution to be separately sprayed onto upper and lower sides of the silicone shell 20.

The organic chemical solution used in the silicone etching step (step S30) may be selected from at least one of xylene, toluene, benzene, and a cyclic aromatic compound.

In the silicone etching step (step S30), at least one microsprayer 58 may be disposed in the lower space of the drying device 50 at a position in which the organic chemical solution is uniformly sprayed onto the silicone shell 20 so that thickening of the silicone shell 20 from a lower end thereof is prevented during drying.

The drying device 50 may be configured such that the concentration of the organic chemical solution sprayed from the microsprayer 58 is adjusted as needed. That is, when a thickness difference of the silicone shell 20 is great, the organic chemical solution is sprayed from the microsprayer 58 after increasing the concentration thereof, and thus, the thickness of the silicone shell 20 may be rapidly adjusted using a small amount of the organic chemical solution. On the other hand, when the thickness difference of the silicone shell 20 is small, the concentration of the organic chemical solution is relatively decreased.

The drying device 50 is configured such that a volatilization direction of the organic chemical solution sprayed from the microsprayer is changed and adjusted by adjusting a direction of the dry air from the air blower 55.

For example, when the organic chemical solution is sprayed from the microsprayer 58 only in one direction, the organic chemical solution contacts only a very small local portion of the silicone shell 20. By contrast, the air blower 58 may blow air toward the organic chemical solution upwardly sprayed from the microsprayer 58, from various directions, thereby variously changing the direction of the organic chemical solution. Accordingly, the organic chemical solution may contact the entire surface of the silicone shell 20 or may be moved while in contact with the surface of the silicone shell 20 along the surface thereof so that the silicone shell 20 has an entirely uniform thickness.

In the silicone hardening step (step S40), the silicone solution 5 coated on the mold body 10 that has passed through steps S20 and S30 is hardened by heating in the drying device 50 so as to be substantially formed into the silicone shell 20.

In this regard, a heating time and temperature may vary according to the silicone solution 5 to be used. For example, a solution of HTV silicone may be generally hardened at 175° C. for about 2 hours or longer for complete hardening.

In the mold separation step (step S50), the silicone shell 20 is separated from the mold body 10. First, a central portion of a lower surface of the silicone shell 20 is perforated.

Through the perforated central portion of the silicone shell 20, the silicone shell 20 is separated from the mold body 10 with caution to prevent damage.

In the prosthesis formation step (step S60), which is the final process for obtaining the silicone prosthesis I, the patch part 25 is attached to the perforated central portion of the lower surface of the silicone shell 20. That is, because of the attachment of the patch part 25, the inner space of the silicone shell 20 in which the mold body has been disposed is closed from the outside.

The patch part 25 includes an inlet sealing portion (not shown) for sealing a fine inlet having injection needle holes through which the filling material 30 is filled into the inner space of the silicone shell 20. For the attachment of the patch part 25, a bonding device (not shown) may be used.

The inlet sealing portion and the bonding device may have a structure and operating principle generally used in silicone prostheses and a silicone bonding device, and thus, a detailed description thereof is not provided here.

Figure 10:
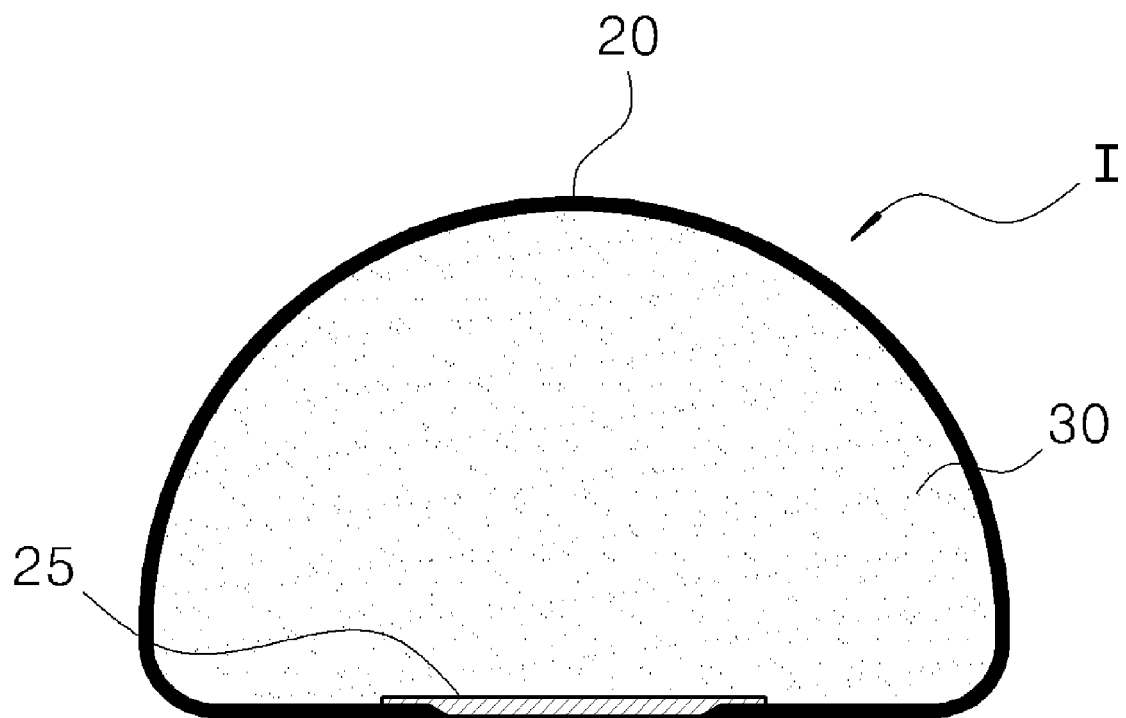
FIG. 10 is a sectional view of a silicone prosthesis according to an embodiment of the present invention.

Lastly, a sufficient amount of the filling material 30 is injected into a hollow inner space of the silicone shell 20, thereby completing manufacture of the silicone prosthesis I as illustrated in FIG. 10.

That is, according to the round or anatomical type silicone prosthesis having a shell with enhanced durability and the manufacturing method thereof, the silicone shell 20 forming an outer appearance of the silicone prosthesis has an outer wall having a uniform thickness without thickness differences. Accordingly, stress concentration may be minimized by eliminating the difference in physical characteristics and stress to thus maximize resistance to fatigue rupture. Moreover, there is no deformation of or damage to products even after extended use of the silicone prosthesis and thus the safety and lifespan of the silicone prosthesis are maximized, which leads to increased product reliability.

In addition, the silicone shell 20 is formed corresponding to types (i.e., round type and anatomical type) and sizes of products, and thus, it may be possible to manufacture a silicone shell having a uniform thickness regardless of various types and sizes of products.

Moreover, the silicone prosthesis I has a smoothly and forwardly curved surface and a uniform and small thickness and thus may have excellent texture, excellent comfort when implanted into the body, and improved product quality.

Furthermore, overall manufacturing processes for forming the silicone shell 20 are automated, which results in productivity improvement, reduced personnel expenses, convenience of operation, quality reproducibility, and maximized product quality.

Figure 11:
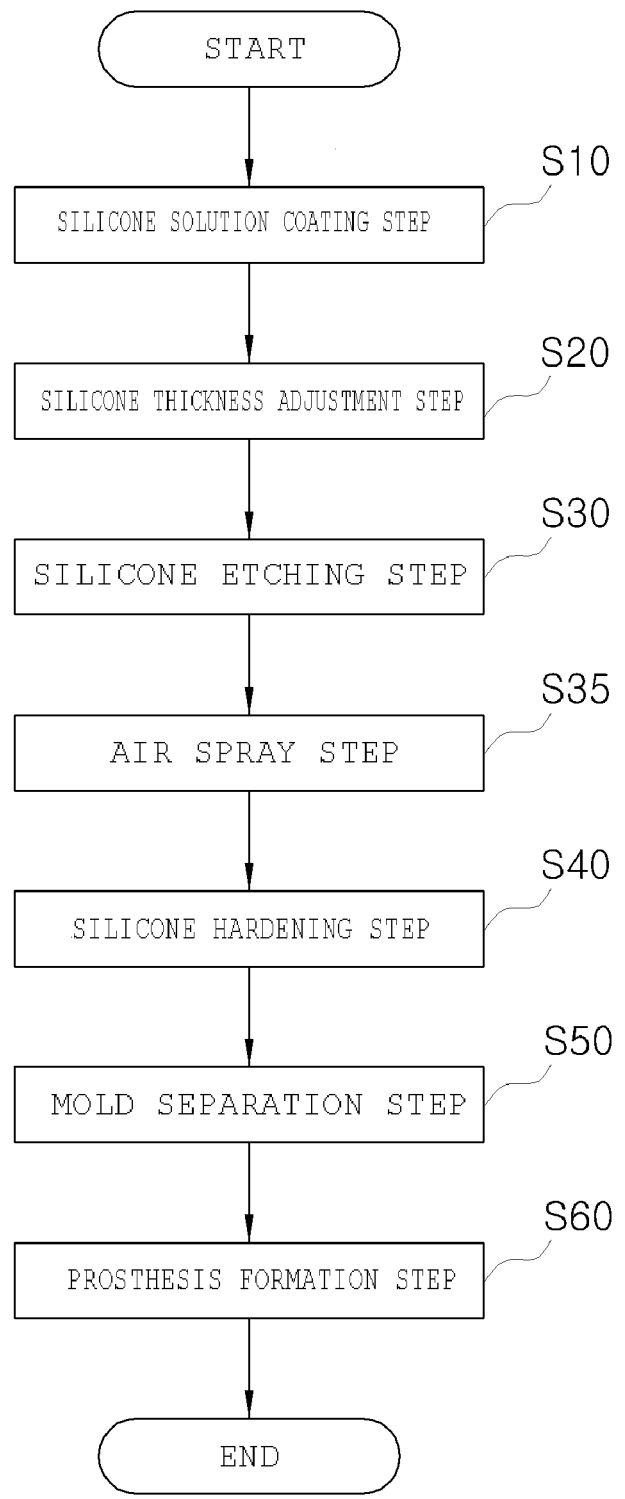
FIG. 11 is a flowchart illustrating a round or anatomical type silicone prosthesis manufacturing method according to another embodiment of the present invention.

According to another embodiment, the method of manufacturing the round or anatomical type silicone prosthesis having a shell with enhanced durability may further include, as illustrated in FIG. 11, an air spray step (step S35) performed before the silicone hardening step (step S40).

The air spray step (step S35) is performed between the silicone solution coating step (step S10) and the silicone hardening step (step S40). In the air spray step (step S35), the silicone solution 5 coated on the mold body 10 is blown using a high pressure air nozzle (not shown) to completely attach the silicone solution 5 to the mold body 10 in accordance with the shape thereof. That is, air is uniformly sprayed onto the silicone solution 5 via an air nozzle for ejecting high pressure air, such as an air gun, at a position proximate to the silicone solution 5, whereby the silicone solution 5 is closely attached to the mold body 10.

That is, when the manufacturing method including the air spray step (step S35) is used, a drying process is performed after completely attaching the silicone solution 5 to the surface of the mold body 10 having a shape of the silicone prosthesis, and thus, an adhesive strength between the silicone solution 5 and the mold body 10 is increased and therefore prevents the silicone shell 20 from being detached from the mold body 10 during the drying process. In addition, the size of the silicone prosthesis is accurately standardized, and thus product quality may be improved.

The other steps of the above-described manufacturing method according to another embodiment excluding step S35 are the same as the steps of the manufacturing method according to the embodiment, and thus a detailed description thereof is not provided here.

One or more embodiments of a method of manufacturing a round or anatomical type silicone prosthesis having a shell with enhanced durability will now be described more fully with reference to Examples 1 through 6.

Example 1

1. First, a round type mammary mold body having a volume of 300 cc was washed with clean water, air brushed, mounted on a jig inside a drying device, and then dried.
2. A dispersion having a viscosity of approximately 900 cPs containing HTV type silicone gum having an average molecular weight of 600,000 to 1,000,000 in xylene as a solvent was prepared.
3. The mold body was completely immersed in the prepared dispersion to coat a surface of the mold body with the dispersion.
4. A horizontal axis rotational velocity of the jig was adjusted to 20 rpm and tilting angles of the jig downward based on a level surface were set to 25° in front, rear, left and right directions, to apply rotation and tilting movements to the mold body.
5. In this regard, average temperatures of inner upper and lower parts of the drying device based on a barrier member were set to approximately 50° C. and approximately 40° C., respectively, and air velocities of the inner upper and lower parts of the drying device were set to about 0.5 m/sec and about 0.2 m/sec, respectively. Then, a drying process was performed for 30 minutes.
6. 4 minutes after the drying process described in 5 above, fine spraying of about 10 ml of xylene as an organic solvent was performed to a lower section of the drying device via a sprayer.
7. The processes described in 3 through 5 above were repeated five times to perform a total of six coating processes.
8. The mold body completely coated with the dispersion (i.e., the silicone solution) was heated at 175° C. for 2 hours to harden the formed silicone shell.
9. The silicone shell was separated from the mold body, a thickness deviation of the silicone shell was measured, a patch part was attached to the silicone shell, and a filling material was filled into an inner space of the silicone shell, thereby completing the manufacture of the silicone mammary prosthesis.

Table 1 below shows measurement results of the thickness of each of a plurality of portions of the silicone shell prepared according to Example 1.

TABLE 1

| Points | Apex (mm) | Radius (mm) | Base (mm) |
|---|---|---|---|
| 1 | 0.60 | 0.59 | 0.60 |
| 2 | 0.60 | 0.59 | 0.60 |

TABLE 1-continued

| Points | Apex (mm) | Radius (mm) | Base (mm) |
|---|---|---|---|
| 3 | 0.61 | 0.60 | 0.60 |
| 4 | 0.61 | 0.60 | 0.59 |
| 5 | 0.61 | 0.60 | 0.59 |
| 6 | 0.60 | 0.59 | 0.58 |
| 7 | 0.60 | 0.59 | 0.60 |
| 8 | 0.60 | 0.58 | 0.61 |
| 9 | 0.60 | 0.59 | 0.62 |
| 10 | 0.60 | 0.59 | 0.59 |
| Average | 0.60 | 0.59 | 0.60 |

Example 2

1. First, a round type mammary mold body having a volume of 300 cc was washed with clean water, air brushed, mounted on a jig inside a drying device, and then dried.
2. A dispersion having a viscosity of approximately 300 cPs containing HTV type silicone gum having an average molecular weight of 600,000 to 1,000,000 in xylene as a solvent was prepared.
3. The prepared dispersion was sprayed onto the mold body through a sprayer to coat the entire surface of the mold body with the dispersion.
4. A horizontal axis rotational velocity of the jig was adjusted to 20 rpm and tilting angles of the jig downward based on a level surface were set to 25° in front, rear, left and right directions, to apply rotation and tilting movements to the mold body.
5. In this regard, average temperatures of inner upper and lower parts of the drying device based on a barrier member were set to approximately 50° C. and approximately 40° C., respectively, and air velocities of the inner upper and lower parts of the drying device were set to about 0.5 m/sec and about 0.2 m/sec, respectively. Then, a drying process was performed for 30 minutes.
6. 4 minutes after the drying process described in 5 above was performed, fine spraying of about 10 ml of xylene as an organic solvent was performed to a lower section of the drying device via a sprayer.
7. The processes described in 3 through 5 above were repeated six times to perform a total of seven coating processes.
8. The mold body completely coated with the dispersion (i.e., silicone solution) was heated at 175° C. for 2 hours to harden the formed silicone shell.
9. The silicone shell was separated from the mold body, a thickness deviation of the silicone shell was measured, a patch part was attached to the silicone shell, and a filling material was filled into an inner space of the silicone shell, thereby completing the manufacture of the silicone mammary prosthesis.

Table 2 below shows measurement results of the thickness of each of a plurality of portions of the silicone shell prepared according to Example 2.

TABLE 2

| Points | Apex (mm) | Radius (mm) | Base (mm) |
|---|---|---|---|
| 1 | 0.48 | 0.48 | 0.48 |
| 2 | 0.48 | 0.48 | 0.48 |
| 3 | 0.49 | 0.49 | 0.47 |
| 4 | 0.49 | 0.50 | 0.48 |
| 5 | 0.50 | 0.50 | 0.47 |
| 6 | 0.50 | 0.51 | 0.47 |
| 7 | 0.49 | 0.48 | 0.48 |

TABLE 2-continued

| Points | Apex (mm) | Radius (mm) | Base (mm) |
| --- | --- | --- | --- |
| 8 | 0.49 | 0.49 | 0.48 |
| 9 | 0.48 | 0.49 | 0.48 |
| 10 | 0.48 | 0.50 | 0.48 |
| Average | 0.49 | 0.49 | 0.48 |

Example 3

1. First, a round type mammary mold body having a volume of 300 cc was washed with clean water, air brushed, mounted on a jig inside a drying device, and then dried.
2. A dispersion having a viscosity of approximately 900 cPs containing HTV type silicone gum having an average molecular weight of 600,000 to 1,000,000 in xylene as a solvent was prepared.
3. The mold body was completely immersed in the prepared dispersion to coat a surface of the mold body with the dispersion.
4. A horizontal axis of the jig was not in a rotation state and tilting angles of the jig downward based on a level surface were set to 25° in front, rear, left and right directions, to apply rotation and tilting movements to the mold body.
5. In this regard, average temperatures of inner upper and lower parts of the drying device based on a barrier member were set at approximately 50° C. and approximately 40° C., respectively, and air velocities of the inner upper and lower parts of the drying device were set at about 0.5 m/sec and about 0.2 m/sec, respectively. Then, a drying process was performed for 30 minutes.
6. 4 minutes after the drying process of the processes described in 5 above was performed, fine spraying of about 10 ml of xylene as an organic solvent was performed to a lower section of the drying device via a sprayer.
7. The processes described in 3 through 5 above were repeated five times to perform a total of six coating processes.
8. The mold body completely coated with the dispersion (i.e., silicone solution) was heated at 175° C. for 2 hours to harden the formed silicone shell.
9. The silicone shell was separated from the mold body, a thickness deviation of the silicone shell was measured, a patch part was attached to the silicone shell, and a filling material was filled into an inner space of the silicone shell, thereby completing the manufacture of the silicone mammary prosthesis.

Table 3 below shows measurement results of the thickness of each of a plurality of portions of the silicone shell prepared according to Example 3.

TABLE 3

| Points | Apex (mm) | Radius (mm) | Base (mm) |
| --- | --- | --- | --- |
| 1 | 0.61 | 0.59 | 0.60 |
| 2 | 0.62 | 0.58 | 0.61 |
| 3 | 0.61 | 0.60 | 0.60 |
| 4 | 0.61 | 0.60 | 0.63 |
| 5 | 0.62 | 0.61 | 0.61 |
| 6 | 0.61 | 0.60 | 0.58 |
| 7 | 0.60 | 0.60 | 0.60 |
| 8 | 0.61 | 0.59 | 0.62 |
| 9 | 0.60 | 0.59 | 0.57 |
| 10 | 0.61 | 0.60 | 0.58 |
| Average | 0.61 | 0.60 | 0.60 |

Example 4

1. First, a round type mammary mold body having a volume of 300 cc was washed with clean water, air brushed, mounted on a jig inside a drying device, and then dried.
2. A dispersion having a viscosity of approximately 900 cPs containing HTV type silicone gum having an average molecular weight of 600,000 to 1,000,000 in xylene as a solvent was prepared.
3. The mold body was completely immersed in the prepared dispersion to coat a surface of the mold body with the dispersion.
4. A horizontal axis of the jig was not in a rotation state and tilting angles of the jig downward based on a level surface were set to 25° in front, rear, left and right directions, to apply rotation and tilting movements to the mold body. In this regard, jig displacement was set as follows: 180° for 3 minutes only once so that the jig was disposed in a reverse form for 3 minutes at an initial time and returned to an original position.
5. In this regard, average temperatures of inner upper and lower parts of the drying device based on a barrier member were set to approximately 50° C. and approximately 40° C., respectively, and air velocities of the inner upper and lower parts of the drying device were set to about 0.5 m/sec and about 0.2 m/sec, respectively. Then, a drying process was performed for 30 minutes.
6. The processes described in 3 through 5 above were repeated five times to perform a total of six coating processes.
7. The mold body completely coated with the dispersion was heated at 175° C. for 2 hours to harden the formed silicone shell.
8. The silicone shell was separated from the mold body, a thickness deviation of the silicone shell was measured, a patch part was attached to the silicone shell, and a filling material is filled into an inner space of the silicone shell, thereby completing the manufacture of the silicone mammary prosthesis.

Table 4 below shows measurement results of the thickness of each of a plurality of portions of the silicone shell prepared according to Example 4.

TABLE 4

| Points | Apex (mm) | Radius (mm) | Base (mm) |
| --- | --- | --- | --- |
| 1 | 0.60 | 0.59 | 0.61 |
| 2 | 0.62 | 0.59 | 0.62 |
| 3 | 0.61 | 0.60 | 0.60 |
| 4 | 0.61 | 0.60 | 0.63 |
| 5 | 0.62 | 0.61 | 0.61 |
| 6 | 0.61 | 0.60 | 0.63 |
| 7 | 0.59 | 0.63 | 0.62 |
| 8 | 0.61 | 0.60 | 0.61 |
| 9 | 0.60 | 0.59 | 0.61 |
| 10 | 0.60 | 0.58 | 0.61 |
| Average | 0.61 | 0.60 | 0.62 |

Example 5

1. First, an anatomical type mammary mold body having a volume of 330 cc was washed with clean water, air brushed, mounted on a jig inside a drying device, and then dried. In this regard, the mold body was mounted on the jig in a state of being tilted at 15° in a direction as illustrated in FIG. 7 based on a level surface.
2. A dispersion having a viscosity of approximately 900 cPs containing HTV type silicone gum having an average molecular weight of 600,000 to 1,000,000 in xylene as a solvent was prepared.

3. The mold body was completely immersed in the prepared dispersion to coat a surface of the mold body with the dispersion.

4. A horizontal axis of the jig was not in a rotation state and tilting angles of the jig downward based on a level surface were set at 25° in front, rear, left and right directions, to apply rotation and tilting movements to the mold body.

5. In this regard, average temperatures of inner upper and lower parts of the drying device based on a barrier member were set at approximately 50° C. and approximately 40° C., respectively, and air velocities of the inner upper and lower parts of the drying device were set at about 0.5 m/sec and about 0.2 m/sec, respectively. Then, a drying process was performed for 30 minutes.

6. 4 minutes after the drying process described in 5 above was performed, fine spraying of about 10 ml of xylene as an organic solvent was performed to a lower section of the drying device via a sprayer.

7. The processes described in 3 through 5 above were repeated five times to perform a total of six coating processes.

8. The mold body completely coated with the dispersion (i.e., silicone solution) was heated at 175° C. for 2 hours to harden the formed silicone shell.

9. The silicone shell was separated from the mold body, a thickness deviation of the silicone shell was measured, a patch part was attached to the silicone shell, and a filling material was filled into an inner space of the silicone shell, thereby completing the manufacture of the silicone mammary prosthesis.

Table 5 below shows measurement results of the thickness of each of a plurality of portions of the silicone shell prepared according to Example 5.

TABLE 5

| Points | Apex (mm) | Radius (mm) | Base (mm) |
| --- | --- | --- | --- |
| 1 | 0.63 | 0.62 | 0.61 |
| 2 | 0.63 | 0.62 | 0.62 |
| 3 | 0.62 | 0.63 | 0.61 |
| 4 | 0.61 | 0.63 | 0.62 |
| 5 | 0.60 | 0.64 | 0.60 |
| 6 | 0.60 | 0.63 | 0.57 |
| 7 | 0.61 | 0.62 | 0.59 |
| 8 | 0.61 | 0.62 | 0.62 |
| 9 | 0.63 | 0.63 | 0.61 |
| 10 | 0.63 | 0.63 | 0.59 |
| Average | 0.62 | 0.63 | 0.60 |

Example 6

1. First, an anatomical type mammary mold body having a volume of 330 cc was washed with clean water, air brushed, mounted on a jig inside a drying device, and then dried. In this regard, the mold body was mounted on the jig in a state of being tilted at 15° in a direction as illustrated in FIG. 7 based on a level surface.

2. A dispersion having a viscosity of approximately 900 cPs containing HTV type silicone gum having an average molecular weight of 600,000 to 1,000,000 in xylene as a solvent was prepared.

3. The mold body was completely immersed in the prepared dispersion to coat a surface of the mold body with the dispersion.

4. A horizontal axis of the jig was not in a rotation state and tilting angles of the jig downward based on a level surface were set at 25° in front, rear, left and right directions, to apply rotation and tilting movements to the mold body. In this regard, jig displacement was set as follows: 180° for 3 minutes only once so that the jig was disposed in a reverse form for 3 minutes at an initial time and returned to an original position.

5. In this regard, average temperatures of inner upper and lower parts of the drying device based on a barrier member were set to approximately 50° C. and approximately 40° C., respectively, and air velocities of the inner upper and lower parts of the drying device were set to about 0.5 m/sec and about 0.2 m/sec, respectively. Then, a drying process was performed for 30 minutes.

6. The processes described in 3 through 5 above were repeated five times to perform a total of six coating processes.

7. The mold body completely coated with the dispersion was heated at 175° C. for 2 hours to harden the formed silicone shell.

8. The silicone shell was separated from the mold body, a thickness deviation of the silicone shell was measured, a patch part was attached to the silicone shell, and a filling material was filled into an inner space of the silicone shell, thereby completing the manufacture of the silicone mammary prosthesis.

Table 6 below shows measurement results of the thickness of each of a plurality of portions of the silicone shell prepared according to Example 6.

TABLE 6

| Points | Apex (mm) | Radius (mm) | Base (mm) |
| --- | --- | --- | --- |
| 1 | 0.62 | 0.62 | 0.61 |
| 2 | 0.61 | 0.62 | 0.62 |
| 3 | 0.62 | 0.63 | 0.62 |
| 4 | 0.60 | 0.63 | 0.63 |
| 5 | 0.60 | 0.61 | 0.62 |
| 6 | 0.63 | 0.63 | 0.62 |
| 7 | 0.62 | 0.61 | 0.61 |
| 8 | 0.61 | 0.62 | 0.63 |
| 9 | 0.62 | 0.63 | 0.61 |
| 10 | 0.63 | 0.62 | 0.63 |
| Average | 0.62 | 0.62 | 0.62 |

The thicknesses of the shell at 10 points of each of the apex, radius and bottom of the shell were measured, which is a shell thickness measurement method commonly used in the art, and measurement results are shown in Tables 1 through 6.

As shown in Tables 1 through 6, it can be confirmed that while a difference in total thickness of the shell occurs according to each of the manufacturing methods and the viscosity of a raw material used, all the silicone prostheses of Examples 1 through 6 have a uniform thickness such that the thickness of each part of the shell is entirely uniform (thickness deviation between the thickest part and the thinnest part of the shell is within 5%).

Also, a 300 cc round type shell was manufactured using the same raw material as that used in Examples 1 to 6 using a conventional simple drying method, and measurement results of the thickness of each part of the shell are shown in Table 7. In this regard, thickness deviation between the thickness portion and the thinnest portion of the shell is approximately 55.5%.

Table 7 below shows measurement results of the thickness of each part of the round type shell manufactured using a conventional simple drying method.

TABLE 7

| Points | Apex (mm) | Radius (mm) | Base (mm) |
|---|---|---|---|
| 1 | 0.55 | 0.57 | 0.88 |
| 2 | 0.57 | 0.58 | 0.85 |
| 3 | 0.56 | 0.56 | 0.85 |
| 4 | 0.58 | 0.55 | 0.87 |
| 5 | 0.55 | 0.54 | 0.88 |
| 6 | 0.57 | 0.54 | 0.86 |
| 7 | 0.57 | 0.56 | 0.86 |
| 8 | 0.58 | 0.55 | 0.86 |
| 9 | 0.57 | 0.55 | 0.87 |
| 10 | 0.57 | 0.57 | 0.88 |
| Average | 0.57 | 0.56 | 0.87 |

Also, thickness deviation of a shell of a commercially available mammary prosthesis known to be manufactured using a conventional rotary drying method was analyzed, and measurement results of the thickness of each part of the shell are shown in Table 8. In this regard, thickness deviation between the thickest portion and the thinnest portion of the shell is approximately 19.8%.

Table 8 below shows measurement results of the thickness of each part of the round type shell manufactured using the conventional rotary drying method.

TABLE 8

| Point | Apex (mm) | Radius (mm) | Base (mm) |
|---|---|---|---|
| 1 | 0.59 | 0.51 | 0.49 |
| 2 | 0.58 | 0.49 | 0.46 |
| 3 | 0.56 | 0.46 | 0.46 |
| 4 | 0.54 | 0.47 | 0.46 |
| 5 | 0.61 | 0.46 | 0.47 |
| 6 | 0.55 | 0.48 | 0.47 |
| 7 | 0.57 | 0.45 | 0.48 |
| 8 | 0.57 | 0.45 | 0.49 |
| 9 | 0.58 | 0.50 | 0.49 |
| 10 | 0.54 | 0.48 | 0.48 |
| Average | 0.57 | 0.48 | 0.48 |

From the results shown in Table 8, it can be confirmed that the shell of the silicone prosthesis manufactured using the manufacturing method according to the present invention has a smaller thickness deviation as compared to the silicone prostheses manufactured using the conventional methods.

As is apparent from the above description, according to a round or anatomical type silicone prosthesis having a shell with enhanced durability and the manufacturing method thereof, the silicone shell forming an outer appearance of the silicone prosthesis has an entirely uniform thickness without thickness deviation and thus stress concentration may be minimized by eliminating the difference in physical characteristics and stress to thus maximize resistance to fatigue rupture. Moreover, there is no deformation of or no damage to products even after long-term use of the silicone prosthesis and thus the safety and lifespan of the silicone prosthesis are maximized, which leads to increased reliability for the use of the products.

In addition, according to the round or anatomical type silicone prosthesis having a shell with enhanced durability and the manufacturing method thereof, the silicone shell is manufactured by coating a mold body with a silicone solution and drying the resulting mold body, corresponding to the types and size of products, i.e., silicone prostheses of a round or anatomical type, and thus has a uniform thickness regardless of various shapes and sizes of products.

In addition, according to the round or anatomical type silicone prosthesis having a shell with enhanced durability and the manufacturing method thereof, the silicone prosthesis has a smoothly and forwardly curved surface and a uniform and small thickness and thus has superior texture and comfort when implanted into the body and improved product quality.

Moreover, according to the round or anatomical type silicone prosthesis having a shell with enhanced durability and the manufacturing method thereof, overall manufacturing processes for forming the silicone shell are automated, which results in productivity improvement, reduced personnel expenses, convenience of operation, quality reproducibility, and maximized product quality.

Furthermore, according to the round or anatomical type silicone prosthesis having a shell with enhanced durability and the manufacturing method thereof, a drying process is performed after completely attaching the silicone solution to the surface of the mold body having a shape of the silicone prosthesis, and thus, an adhesive strength between the silicone solution and the mold body is increased and therefore prevents the silicone shell from being detached from the mold body during the drying process. In addition, the size of the silicone prosthesis is accurately standardized, and thus the quality of products may be improved.

Although the preferred embodiments of a round or anatomical type silicone prosthesis having a shell with enhanced durability and a manufacturing method thereof have been disclosed for illustrative purposes, those skilled in the art will appreciate that various modifications, additions and substitutions are possible, without departing from the scope and spirit of the invention as disclosed in the accompanying claims.

What is claimed is:

1. A method of manufacturing a round or anatomical type silicone prosthesis comprising a silicone shell, the method comprising the steps of:
   coating a silicone solution on a mold body having a shape of the silicone prosthesis;
   drying the coated mold body in a drying device to form the silicone shell;
   during the drying step, adjusting a silicone thickness in a manner such that a jig is disposed in an inner space of the drying device to fix the mold body, the mold body is fixed to the jig, and the jig is then continuously rotated and tilted at various angles to uniformly adjust the thickness of the silicone shell using fluidity of silicone, wherein, in the silicone thickness adjustment step, the jig of the drying device is periodically or non-periodically tilted within a predetermined angle in all directions including front, rear, left and right directions while securing the mold body so that it does not self-rotate on a longitudinal axis of the jig;
   a silicone etching step using a barrier member included in the drying device to define upper and lower spaces of the drying device and spraying an organic chemical solution onto the silicone shell through a microsprayer;
   a silicone hardening step to harden the resulting mold body to form the silicone shell; and
   a mold separation step to separate the silicone shell from the mold body.

2. The method according to claim 1, wherein in the silicone thickness adjustment step the jig of the drying device further comprises a jig displacement configuration such that the jig rotates or revolves about a center axis at a revolution angle ranging from 1 to 360° and is continuously revolved by repeating a temporary stop at every determined angle within 1 to 180° among rotation displacements for a certain period of time.

3. The method according to claim 1, wherein the silicone solution coating step is performed by immersing the mold body having the shape of the silicone prosthesis in a vessel filled with a sufficient amount of the silicone solution or spraying the silicone solution onto the mold body;

wherein the mold separation step to separate the silicone shell from the mold body is performed through a perforated lower surface portion of the silicone shell.

4. The method according to claim 1, wherein the drying device is configured such that dry air is uniformly blown from all directions including up, down, left and right directions through an air blower, the method further comprising setting a temperature difference between upper and lower spaces of the drying device such that temperatures in the upper and lower spaces are differently adjusted.

5. The method according to claim 1, wherein drying device controls a drying rate of the silicone shell by adjusting an amount and velocity of air from the air blower and thus the thickness of the silicone shell may be entirely adjusted.

6. The method according to claim 1, wherein organic chemical solution used in the silicone etching step comprises at least one of xylene, toluene, benzene, and a cyclic aromatic compound.

7. The method according to claim 1, wherein the microsprayer used in the silicone etching step comprises at least one microsprayer disposed in the lower space of the drying device at a position in which the organic chemical solution is uniformly sprayed onto the silicone shell so that thickening of the silicone shell from a lower surface thereof is prevented during drying.

8. The method according to claim 1, wherein the drying device adjusts a concentration of the organic chemical solution sprayed from the microsprayer as needed.

9. The method according to claim 1, wherein drying device is configured such that a volatilization direction of the organic chemical solution sprayed from the microsprayer is changed and adjusted by adjusting a direction of dry air from an air blower.

10. The method according to claim 1, further comprising an air spray step between the silicone solution coating step and the silicone hardening step, to completely attach the silicone solution coated on the mold body to the mold body in accordance with the shape thereof through a high pressure air nozzle.

11. The method according to claim 1, further comprising a prosthesis formation step to attach a patch part to the perforated lower surface portion so as to close an inner space of the silicone shell from the outside and to inject a filling material into the inner space of the silicone shell.

\* \* \* \* \*